United States Patent
Mohajer

(10) Patent No.: US 7,063,664 B2
(45) Date of Patent: Jun. 20, 2006

(54) DISPOSABLE COVER TO A VAGINAL SPECULUM

(76) Inventor: Pooneh Mohajer, 1835 1/2 S. Beverly Glen Blvd., Los Angeles, CA (US) 90025

( * ) Notice: Subject to any disclaimer, the term of this patent is extended or adjusted under 35 U.S.C. 154(b) by 117 days.

(21) Appl. No.: 10/730,307

(22) Filed: Dec. 8, 2003

(65) Prior Publication Data
US 2005/0124860 A1 Jun. 9, 2005

(51) Int. Cl.
*A61B 1/267* (2006.01)
(52) U.S. Cl. .................. 600/186; 600/184; 600/203; 600/220
(58) Field of Classification Search .......... 600/184, 600/186, 201, 203, 219, 220, 121, 235
See application file for complete search history.

(56) References Cited

U.S. PATENT DOCUMENTS

| 3,841,317 | A | 10/1974 | Awais | 128/17 |
| 4,492,220 | A | 1/1985 | Hayes | 128/17 |
| 4,807,600 | A | 2/1989 | Hayes | 128/17 |
| 5,007,409 | A | 4/1991 | Pope | 128/17 |
| 5,113,873 | A | 5/1992 | Boarman | 128/830 |
| 5,209,241 | A | 5/1993 | Hardy | 128/842 |
| 5,243,966 | A | 9/1993 | Ng | 128/3 |
| 5,325,871 | A | 7/1994 | Reddy | 128/830 |
| 5,460,165 | A | 10/1995 | Mayes | 600/186 |
| 5,515,862 | A | 5/1996 | Artsi et al. | 128/830 |
| 6,036,638 | A | 3/2000 | Nwawka | 600/186 |
| 6,432,048 | B1 * | 8/2002 | Francois | 600/220 |

* cited by examiner

Primary Examiner—Beverly M. Flanagan
(74) Attorney, Agent, or Firm—Gifford, Krass, Groh, Sprinkle, Anderson & Citkowski, P.C.

(57) ABSTRACT

A disposable cover for the opposed blades of a vaginal speculum comprises a tube of sheet plastic or elastomeric material having an opening at one end of the tube to receive the opposed blades of a speculum and pouches adjacent to the open opposite end of the tube for receiving the tips of the speculum blades to prevent rolling back of the sheet tube during vaginal inspection. The ends of the tube adjacent to the pouches terminate in resilient pointed tips to ease insertion of the covered blades in the vaginal area. The sheet cover is preferably prelubricated for ease of use and to eliminate excess lubricant interfering with cervical cytology results or microbiology studies.

10 Claims, 2 Drawing Sheets

DISPOSABLE COVER TO A VAGINAL SPECULUM

BACKGROUND OF THE INVENTION

1. Field of the Invention

The present invention relates to a sheet cover for the blades of a vaginal speculum and more particularly to a tubular cover, adapted to surround both blades of a two-bladed speculum and having pouches on the opposed sides of the interior of the distal end, adapted to receive the ends of the speculum blades, and terminating in resilient pointed tips to aid insertion of the covered speculum.

2. Background Art

Vaginal speculums are widely used during examination and treatment of the vagina and related areas. The speculum gives the examining physician a clear view of the vaginal cavity and prevents vaginal walls from collapsing during medical procedures such as laser surgery and loop electrical excision procedure, in which contact must be avoided between the vaginal walls and the laser or electrode used during such procedures.

A variety of disposable covers have been proposed for speculum blades. These covers minimize the possibility of spread of infectious disease through use of the same speculum with successive patients and minimize the need for resterilization of the speculum between uses. These devices have typically employed separate covers for each of the two blades of the speculum. U.S. patents describing these separate black covers include Hayes U.S. Pat. No. 4,807,600; Pope U.S. Pat. No. 5,007,409 and Mayes U.S. Pat. No. 5,460,165.

Nwawka U.S. Pat. No. 6,036,638 discloses a singular tubular sleeve used to cover both blades of a two-blade vaginal speculum. The distal end of the cover is closed and in order to provide the physician with a view of the vaginal cavity beyond the ends of the blades, a small central hole has been provided in the distal end of the cover. This tubular arrangement is advantageous over arrangements that provide separate covers for each blade in that it supports the side vaginal walls during examination, preventing them from collapsing into the area between the two speculum blades. However, the limited visibility provided through the central hole in the distal wall of the cover unduly limits the physician's view into the vaginal area beyond the termination of the blades. Were this distal wall to be removed, providing a simple tubular cover with open ends, the cover would tend to roll backward on the blades during insertion, obviating the advantages of the cover.

SUMMARY OF THE INVENTION

The present invention is accordingly directed toward a generally tubular cover for a two-bladed speculum, formed of a flexible sheet material such as plastic, and having a slightly enlarged diameter at the proximal end to allow insertion of the speculum blades and a substantially open distal end. To prevent the cover from retracting on the blades during vaginal insertion of the speculum, two elongated pouches are provided adjacent to diametrically opposed points on the distal end of the tubular cover. In a preferred embodiment the pouches are formed on the interior wall of the tube, but they could be formed on the exterior. Each of the pouches has an extension in the direction of the central axis of the tube with an opening directed toward the proximal end, and terminates in a closed wall at the distal end. The pouches are shaped to accept the free ends of the two speculum blades and engage them so as to prevent any rollback of the cover during insertion of the speculum into the inspection area.

To assist insertion of the covered blades into the vagina, the pouches each terminate in a pointed resilient structure preferably formed of the same material as the tube. The pointed tube ends may be easily inserted into the vaginal opening and will guide the easy insertion of the blades into an examination position.

At least the exterior surface of the sheet cover is preferably precoated with a vaginal lubricant. This eliminates the need for prelubricating the vaginal area before insertion of the speculum and thus avoids the problem of excess lubricant interfering with cervical cytology results or microbiology studies. The prelubricating also simplifies the entire process and results in cost and time savings.

Use of the tubular sheet cover of the present invention results in excellent exposure of the entire cervix and cul-de-sacs thus making any surgical procedure to the cervix, such as colposcopy, cervical and vaginal biopsy, cryotherapy, LEEP (Loop Electrical Excision Procedure), LLETZ (Large LEEP Excision Transformation Zone) and laser surgery easier and more accurate because of the improved visibility and accessibility of the cervix and elimination of damage to the sidewalls during these procedures.

The cover of the present invention allows full visualization of the vaginal apex without the need for either a four-bladed speculum or a lateral vaginal retractor, which both push the sidewall of the vaginal canal away from the visual field. These devices are difficult for use by physicians and sometimes painful for the patient. The present invention allows full visualization with a conventional two-bladed speculum.

Other objects, advantages and applications of the present invention will be made apparent by the following detailed description of a preferred embodiment of the invention.

BRIEF DESCRIPTION OF THE DRAWINGS

The specification makes reference to the following drawings in which.

DETAILED DESCRIPTION OF THE PREFERRED EMBODIMENT OF THE INVENTION

Figure 1:
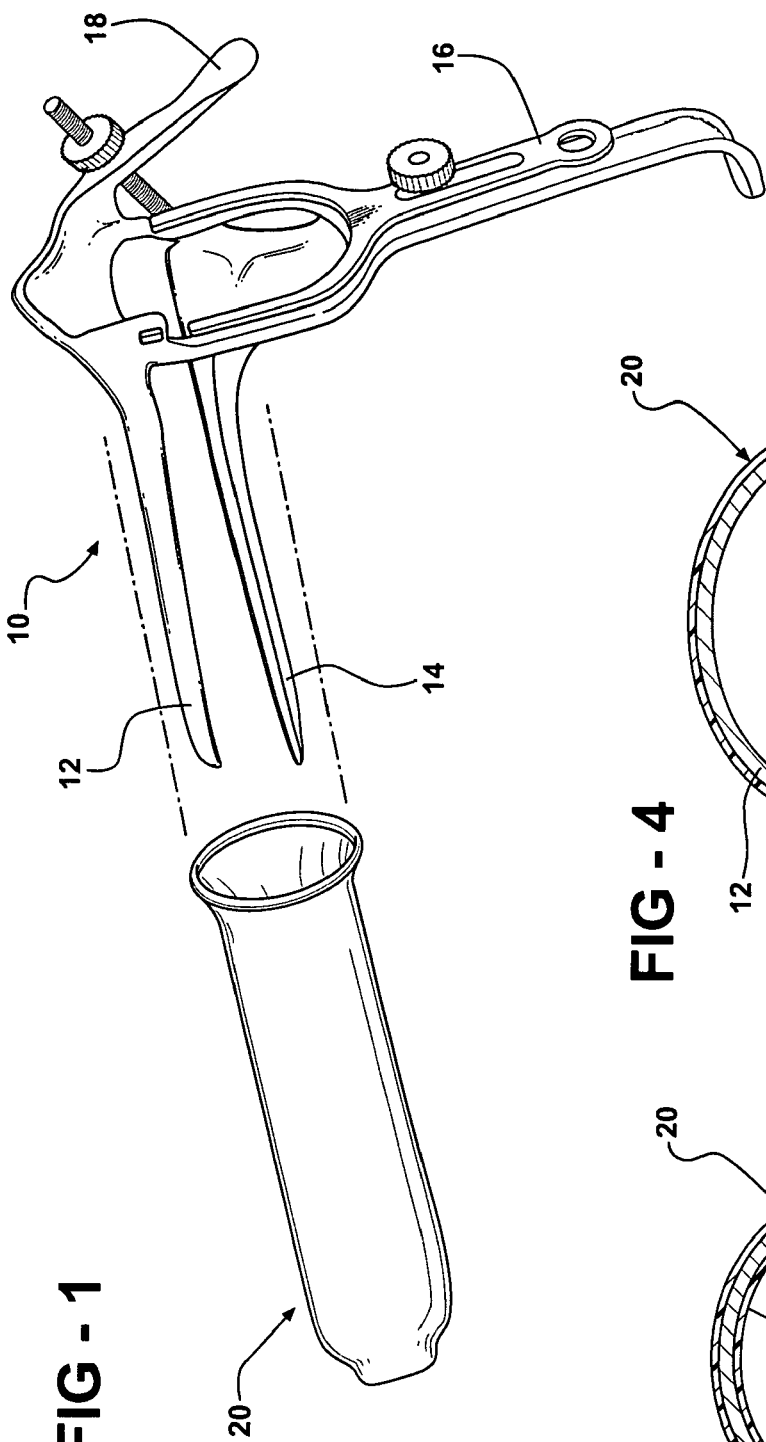
FIG. 1 is an exploded perspective view of a vaginal speculum and a cover forming the preferred embodiment of the present invention displaced from the speculum and positioned to be inserted over the blades of the speculum.
Figure 4:
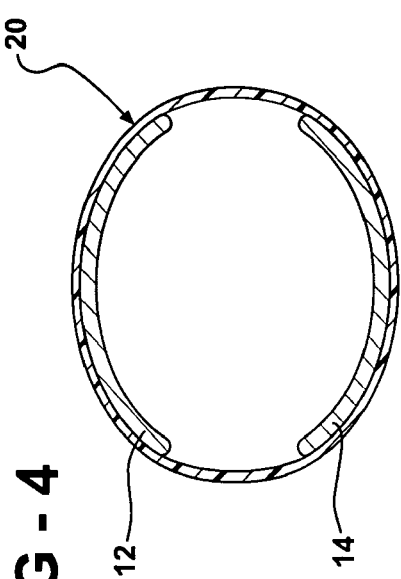
FIG. 4 is a cross-sectional view through the speculum blades and cover taken along lines 4—4 of FIG. 2.
Figure 3:
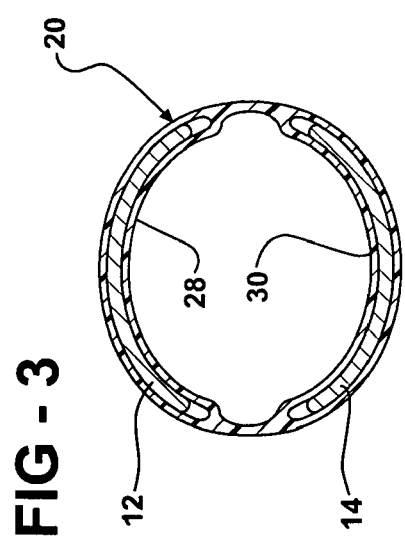
FIG. 3 is a cross-sectional view through the speculum and cover taken along lines 3—3 of FIG. 2.
Figure 2:
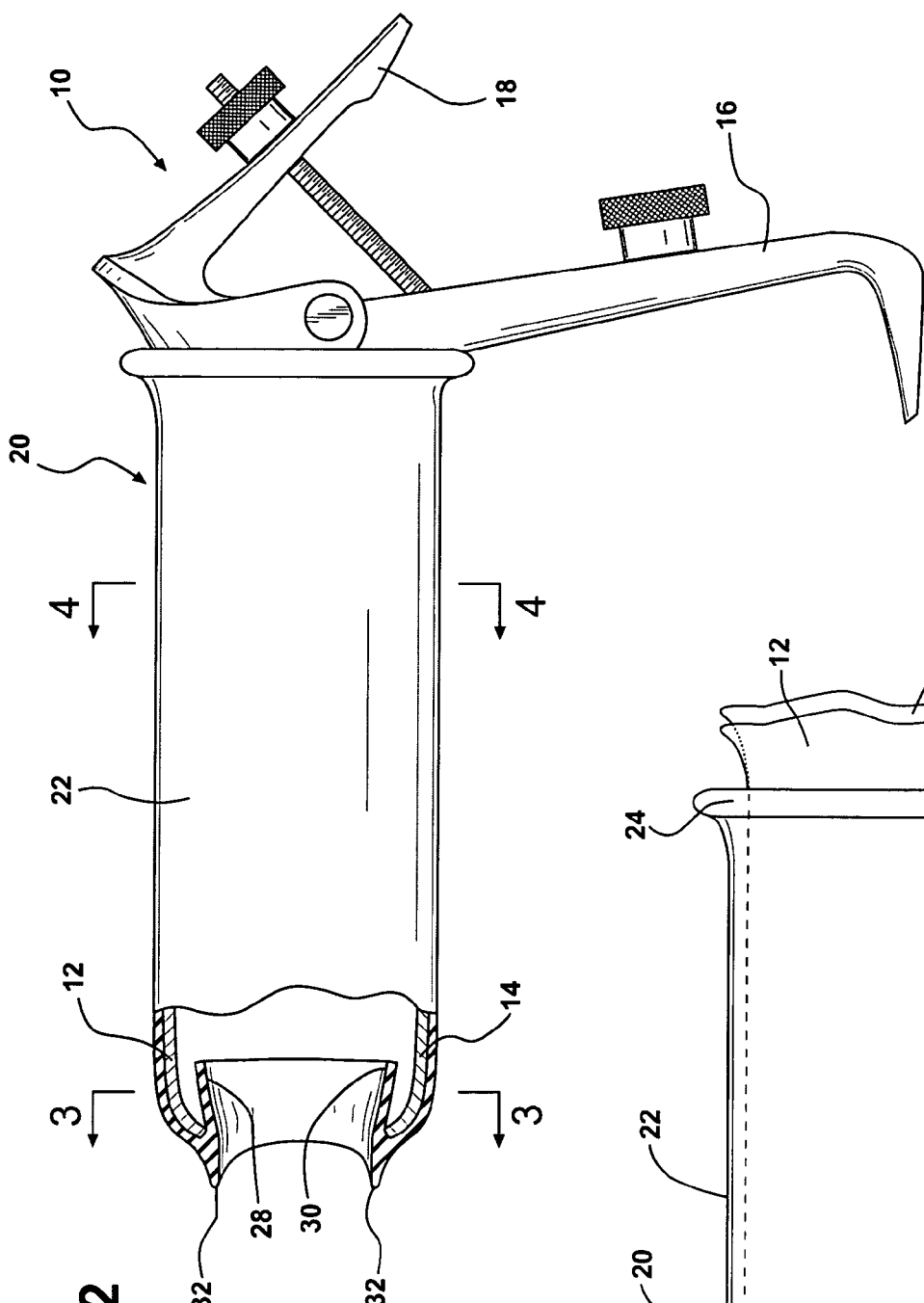
FIG. 2 is a side view of a speculum with the cover of the present invention disposed over the blades and with the cover shown in partial broken-away view.
Figure 5:
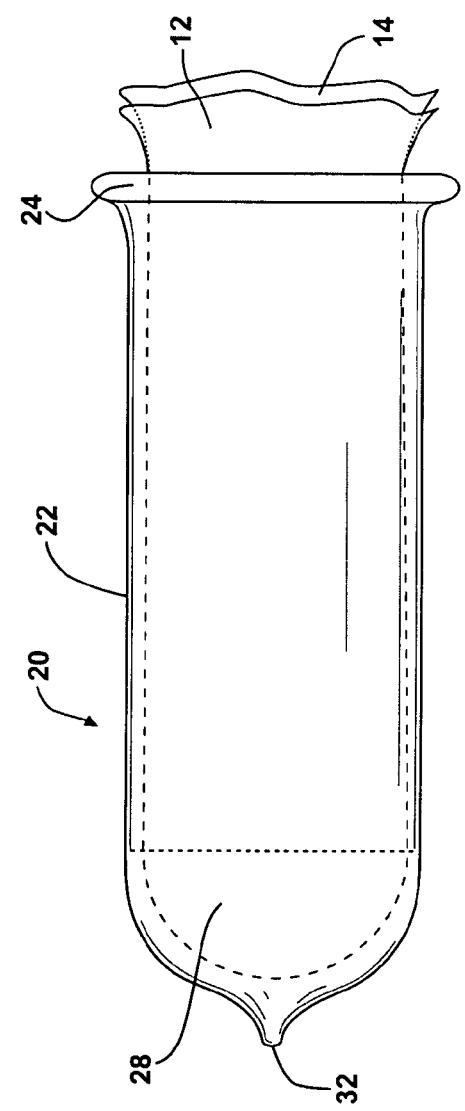
FIG. 5 is a top view of the cover sheet with the speculum blades inserted within the cover.

The cover of the present invention is designed to be used with a vaginal speculum, generally indicated at 10, having a pair of opposed parallel blades 12 and 14. A handle 16 is formed integrally with the blade 14 and a thumb press 18 may be used to pivot the blade 12 away from the blade 14 about a pivot axis located at their proximal ends.

The speculum blade cover of the present invention, generally indicated at 20, comprises a tubular body 22 formed of a thin sheet of latex, an elastomer, or the like which is substantially flexible. The tubular section has a sufficient diameter to enable the speculum blades 12 and 14 to fully separate. The tubular body is slightly enlarged in diameter and cuffed at the proximal end 24. The cuffed proximal end 24 surrounds an opening which allows the speculum blades 12 and 14 to be inserted within the tubular body. The distal end 26 of the tubular body 22 is fully opened. This provides an unobstructed view for the physician observing through the area between the proximal ends of the blades 12 and 14.

A pair of elongated, longitudinally extending pouches 28 and 30 are formed along the interior of the tube 22 at diametrically opposed locations at the proximal end 26. The proximal ends of these pouches 28 and 30 are opened to receive the tips of the blades 12 and 14. The sides of the pouches are sealed to the interior wall of the tube and the distal ends of the pouches 28 and 30 are sealed to the walls of the opening 26.

The pouch sections 28 and 30 of the tube 22 terminate in thickened, soft, pointed tips 32 and 34. The tips are pointed both in width and depth and act to guide the speculum blades 12 and 14 with the covering sheet 20 into the vagina.

The tube 22 could be reinforced with thickened ribs, extending either longitudinally, circumferentially or some combination thereof.

The cover 20 may be precoated, at least on the exterior side, with a vaginal lubricant such as K-Y gel to facilitate the insertion of the speculum blades with the cover into the vagina. Precoating the blades eliminates the need to prelubricate the vagina and the possibility of excessive lubrication interfering with cytology results or microbiology studies. The prelubricated cover 20 may be packaged within a plastic cover and removed for use.

In use, when the blades 12 and 14 are spread, the sides of the tube 22 between the blades extend between the edges of the blade to prevent lateral movement of the walls of the cervix.

The invention claimed is:

1. A cover for the blades of a two-bladed vaginal speculum, comprising:
   a sheath of a flexible film material having a proximal open end for receiving tips of the speculum blade and an open distal end to allow observation of the vaginal area beyond the distal end, the sheath being tubular in cross-section from its proximal end to its distal end;
   two elongated, longitudinally extending pouches formed on the wall of the tubular sheath at diametrically opposed points terminating in closed sections disposed adjacent to the distal end of the sheath and having openings at their proximal ends to receive the tips of the two speculum blades; and
   distally pointed tips formed on the sheath forward of the distal ends of each of the pouches adapted to guide the speculum blades, encased in the pouches, into the vagina.

2. The speculum cover of claim 1 wherein the exterior of the cover is prelubricated with a vaginal lubricant.

3. The speculum cover of claim 1 including an enlarged diameter section at the proximal end to ease the reception of the speculum blades.

4. The speculum cover of claim 1 wherein the sheet material constitutes latex.

5. The speculum cover of claim 1 wherein the pouches are formed on the interior of wall of the tubular sheath.

6. A sheet cover for two blades of a two-bladed vaginal speculum, comprising:
   a tubular section;
   an opening in the tubular section at the proximal end to receive the speculum blades;
   an opening at the distal end of the tubular section, extending the full diameter of the tubular section, to allow observation through the speculum; and
   pointed tips disposed at diametrically opposed points on the distal end of the tubular section forward of the distal ends of the speculum blades adapted to guide the tube encasing the blades into the vagina.

7. The sheet cover of claim 6 including a lubricated coating on the exterior of the tubular section.

8. The sheet cover of claim 6 wherein the sheet cover constitutes latex.

9. The sheet cover of claim 6 further including a pair of pouches extending in a longitudinal direction from said tips and having open proximal ends, said pouches being adapted to retain the tips of the speculum blades within the cover during insertion of the covered blades to avoid rollback of the sheet cover on the speculum blades, and terminating in distal ends adjacent the proximal ends of the tips.

10. The sheet cover of claim 9 wherein the pouches are formed on the interior wall of the tubular section.

* * * * *